United States Patent
Ichihara et al.

(10) Patent No.: US 6,891,064 B1
(45) Date of Patent: May 10, 2005

(54) PROCESS FOR PRODUCING FLUOROALKYLCARBOXYLIC ACID

(75) Inventors: Kazuyoshi Ichihara, Settsu (JP); Hirokazu Aoyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/700,494

(22) PCT Filed: May 20, 1999

(86) PCT No.: PCT/JP99/02679

§ 371 (c)(1), (2), (4) Date: Nov. 16, 2000

(87) PCT Pub. No.: WO99/62859

PCT Pub. Date: Dec. 9, 1999

(30) Foreign Application Priority Data

Jun. 3, 1998 (JP) ............................................ 10-154507

(51) Int. Cl.[7] .......................... C07C 51/27; C07C 53/21
(52) U.S. Cl. ...................... 562/540; 562/605
(58) Field of Search ................. 562/540, 605, 562/541

(56) References Cited

U.S. PATENT DOCUMENTS

| | | |
|---|---|---|
| 2,557,282 A | 6/1951 | Hamblet et al. |
| 2,559,629 A | 7/1951 | Berry |
| 3,678,106 A | 7/1972 | Ager |
| 3,678,107 A | 7/1972 | Yonemitsu et al. |

FOREIGN PATENT DOCUMENTS

| | | |
|---|---|---|
| DE | 2 116 212 | 2/1972 |
| JP | 10-502049 | 2/1998 |

OTHER PUBLICATIONS

Baer, Fluoro Alcohols, Industrial and Engineering Chemistry, vol. 51, No. 7, Jul. 1959, 929–930.

Patent Abstracts of Japan, vol. 005, No. 164, Oct. 21, 1981, JP 56 092832, Jul. 27, 1981.

*Primary Examiner*—Paul A. Zucker
(74) *Attorney, Agent, or Firm*—Stites & Harbison PLLC; B. Aaron Schulman

(57) ABSTRACT

The present invention provides a process for producing a fluoroalkylcarboxylic acid of the formula RfCOOH wherein Rf is a $C_{1-16}$ fluoroalkyl group, which comprises oxidizing a fluoroalkyl alcohol of the formula $RfCH_2OH$ wherein Rf is as defined above using nitric acid. The process according to the present invention produces a fluoroalkylcarboxylic acid with high selectivity at low costs.

4 Claims, No Drawings

US 6,891,064 B1

PROCESS FOR PRODUCING FLUOROALKYLCARBOXYLIC ACID

TECHNICAL FIELD

This invention relates to a process for producing a fluoroalkylcarboxylic acid that is a compound industrially useful as a starting material for the production of surfactants, pharmaceuticals, agricultural chemicals.

BACKGROUND ART

Much research has been carried out on methods for synthesizing carboxylic acid. Such methods are one of the important reaction technologies in synthetic organic chemistry. Known reactions for oxidizing alcohols, aldehydes and the like include an oxygen oxidation reaction using a solid catalyst; an oxidation reaction using a chemical oxidizer such as chromic acid, potassium permanganate, nitric acid or the like; and a liquid phase autoxidation reaction. These conventional methods, however, have problems such as high costs of solid catalysts, difficulty in selective conversion to carboxylic acid in some cases, and high toxicity of many chemical oxidizers.

Methods are known for oxidizing a fluoroalkyl alcohol to the corresponding fluoroalkylcarboxylic acid with a comparatively high yield. Such methods include methods using a chemical oxidizer, for example, potassium dichromate/sulfuric acid (T. Hudlicky et al., J. Fluorine Chem., (1992), 59(1), 9–14), potassium permanganate (I. Lehms et al., DD 268685), or nitrogen dioxide (R. M. Scribner, J. Org. Chem., (1964), vol.29, 279–283 or ibid., (1964), vol.29, 284–286); and methods using an organic or inorganic acid copper salt catalyst/alkali/oxygen (I. P. Skibida et al., WO 93/12059). These methods, however, have the following problems. The method using chromic acid or potassium permanganate has waste disposal problems after reaction. According to the method using nitrogen dioxide, the reaction takes 10 hours or more using 2 equivalents of nitrogen dioxide. Moreover, use of an increased amount of nitrogen dioxide and/or a higher reaction temperature will increase byproducts. The oxidation method using an organic or inorganic acid copper salt catalyst/alkali/oxygen only achieves a low selectivity to carboxylic acid and also has separation and purification problems such as difficulty in removal of the catalyst and the solvent after reaction.

Methods for oxidizing a fluoroalkyl alcohol to the corresponding fluoroalkylcarboxylic acid using nitric acid are described, for example, in D. R. Bear, Ind. Eng. Chem., (1959), vol.51, 829–830 and in Y. Desirant, Bull. Sci. acad. roy. Belg., (1929), vol.15, 966–982. However, Desirant reports that the method has the following problems: the reaction requires using about 2.5 equivalents of nitric acid relative to the alcohol and it takes 2.5 days under reflux to complete the reaction. In hydrocarbon oxidation using nitric acid, it is known that oxygen is introduced into the reaction system to reduce the required amount of nitric acid to a stoichiometric amount or less relative to the reaction substrate (John W. Ager, Jr. DE 2116212). Such technique, however, is not known in fluoroalkyl alcohol oxidation using nitric acid.

DISCLOSURE OF INVENTION

A principal object of this invention is to obviate the defects of the conventional production methods and provide a process for producing a fluoroalkylcarboxylic acid with high selectivity at low costs.

The present inventors carried out extensive research in view of the above prior art problems and found that fluoroalkylcarboxylic acids can be produced with high conversion and high selectivity by oxidizing fluoroalkyl alcohols using nitric acid as an oxidizing agent.

The present invention provides the following processes for preparing fluoroalkylcarboxylic acids.

1. A process for producing a fluoroalkylcarboxylic acid of the formula RfCOOH wherein Rf is a $C_{1-16}$ fluoroalkyl group, which comprises oxidizing a fluoroalkyl alcohol of the formula $RfCH_2OH$ wherein Rf is as defined above using nitric acid.
2. The process according to item 1 wherein the oxidation is carried out in the presence of a metal catalyst.
3. The process according to item 2 wherein the metal catalyst is at least one metal selected from the group consisting of iron, nickel, copper and vanadium, or at least one oxide or salt of these metals.
4. The process according to any one of items 1–3 wherein a fluoroalkylcarboxylic acid of the formula RfCOOH wherein Rf is as defined above has been placed and is present in the reaction system at the beginning of the reaction.
5. The process according to any one of items 1–4 wherein oxygen is fed into the reaction system during the reaction.
6. The process according to item 5 wherein oxygen is fed into the reaction system to reduce the required amount of nitric acid to a stoichiometric amount or less relative to the fluoroalkyl alcohol of the formula $RfCH_2OH$ wherein Rf is as defined above.

The method of the present invention comprises converting a fluoroalkyl alcohol into the corresponding fluoroalkylcarboxylic acid by oxidation using nitric acid.

The fluoroalkyl alcohol used in the present invention is represented by the formula $RfCH_2OH$ wherein Rf is a $C_{1-16}$ fluoroalkyl group. Specific examples include fluoroalkyl alcohols represented by $H(CF_2)_nCH_2OH$ or $F(CF_2)_nCH_2OH$ wherein n is an integer of 1 to 16. Of the alcohols represented by $H(CF_2)_nCH_2OH$, preferable are those wherein n is an integer of 2, 4, 6, 8, 10, 12, 14 or 16. Of the alcohols represented by $F(CF_2)_nCH_2OH$, preferable are those wherein n is an integer of 1 to 3.

The nitric acid used in the present invention has a concentration of 5% or higher, preferably 30% to 70%.

The molar ratio of nitric acid to the starting fluoroalkyl alcohol is 2 or less, i.e., a stoichiometric amount or less, and is usually in the range of 0.1 to 2, preferably 0.3 to 1.

The molar ratio of nitric acid to the starting alcohol may vary depending on the starting alcohol. As the fluoroalkyl group of the starting fluoroalkyl alcohol has a longer chain, a larger molar ratio of nitric acid to the fluoroalkyl alcohol is preferred.

The metal catalyst to be used in the present invention is preferably at least one metal such as iron, nickel, copper, vanadium and the like, or at least one oxide or salt of these metals, of which copper powder, iron chloride (II), iron chloride (III), nickel chloride, copper chloride, ammonium vanadate and vanadium oxide (V) are particularly preferred.

The weight ratio of the metal catalyst to the starting alcohol is usually at least 0.000001, preferably in the range of 0.00001 to 0.1. The use of an increased amount of the metal catalyst can reduce the reaction pressure and reaction temperature. An excess of the metal catalyst, however, will convert the reaction product fluoroalkylcarboxylic acid to a metal salt, thus adversely affecting the separation and purification operation.

The reaction is usually carried out at temperatures in the range of 80° C. to 200° C., preferably 100° C. to 150° C.

By the end of the reaction, the reaction pressure may increase to a maximum of 2.5 MPa (gauge pressure). In consideration of the price of the reactor and other factors, it is preferable that the reaction be carried out while controlling the reaction pressure. A preferable method for controlling the reaction pressure comprises supplying oxygen so as to control the reaction pressure to 0.4 to 1.0 MPa (gauge pressure) during the reaction.

Feeding oxygen into the reaction system not only reduces the molar ratio of nitric acid to a fluoroalkyl alcohol but also helps to control the reaction pressure. Furthermore, it is unnecessary to eliminate nitrogen oxides during the reaction. A preferred method for feeding oxygen into the reaction system comprises supplying oxygen at any time when necessary during the reaction.

Oxygen is continuously fed into the reaction system until the conversion of the starting fluoroalkyl alcohol reaches 100%. The required amount of oxygen is 0.7 to 0.9 mole per mole of the starting fluoroalkyl alcohol.

In pressure control using oxygen, it is preferable that as the fluoroalkyl group of the starting fluoroalkyl alcohol has a longer chain, the reaction pressure should be set to a higher value.

When a fluoroalkylcarboxylic acid is placed into the reaction system before reaction so that carboxylic acid is present at the beginning of the reaction, the reaction pressure may be set to a lower value. The amount of the fluoroalkylcarboxylic acid is preferably 0.01 to 2 moles, more preferably 0.1 to 1 mole, per mole of the starting fluoroalkyl alcohol.

The reaction time is usually within the range of about 10 to about 20 hours. As the reaction pressure is set to a higher value, a shorter reaction time will result. When a fluoroalkylcarboxylic acid and/or a metal salt catalyst is present, the reaction time can be reduced to 4 to 8 hours.

Upon completion of the reaction, nitrogen oxides can be removed by a known removal method such as a dry method, a wet method or the like.

When the obtained fluoroalkylcarboxylic acid of the formula RfCOOH is a fluoroalkylcarboxylic acid wherein Rf is a fluoroalkyl group having at least 4 carbon atoms, the reaction mixture separates into two layers of liquids upon completion of the reaction. The upper layer is a nitric acid layer. The fluoroalkylcarboxylic acid in a concentrated form is present in the lower layer.

Fluoroalkylcarboxylic acid, which is the desired compound of the present invention, can be isolated and purified by known methods. Examples of useful procedures are extraction, distillation, recrystallization, column chromatography and the like.

The method according to the present invention obviates the defects of the conventional production methods and produces a fluoroalkylcarboxylic acid with high selectivity at low costs.

BEST MODE FOR CARRYING OUT THE INVENTION

The present invention will be described below in more detail with reference to Examples.

EXAMPLE 1
(A Case in which the Reaction Pressure was Controlled Using Oxygen)

$H(CF_2)_6CH_2OH$ (664.00 g, 2.00 moles), 55% nitric acid (114.55 g, 1.00 mole) and $FeCl_2nH_2O$ (0.0066 g) were placed into an autoclave equipped with a 1000-ml glass pressure vessel, a fluoroplastic upper cover, stirring blades, a thermometer protection tube, a fluoroplastic insert tube, a pressure gauge, a safety valve and a supply line from an oxygen bomb. The mixture was stirred with heating, upon which reaction pressure began to increase. 3.1 hours after the start of heating, the reaction temperature rose to 125 and the reaction pressure increased to 0.6 MPa (gauge pressure; the same hereinafter). From that time, oxygen was fed into the gas phase at various times in an amount of 0.35 g (11.00 mmoles) per oxygen fed process, whereby the reaction pressure was controlled to 0.6 MPa. 6.5 hours after the start of heating, complete consumption of the starting fluoroalkyl alcohol was confirmed by gas chromatography to confirm the completion of the reaction [$H(CF_2)_6CH_2OH$ conversion: 100.0 g.c. % (gas chromatography %; the same hereinafter); $H(CF_2)_6COOH$ selectivity: 100.0 g.c. %]. In total, 46.72 g (1.46 moles) of oxygen was fed into the gas phase by the end of the reaction. After completion of the reaction, oxygen was continuously supplied so as to convert residual nitrogen oxides into nitric acid. Then the residual pressure was released. Because of the reaction mixture being provided in the form of two layers of liquids, 765.78 g of a crude carboxylic acid [$H(CF_2)_6COOH$] was obtained in a concentrated form from the lower layer by means of liquid-liquid separation at the cease of stirring. The crude carboxylic acid was purified by distillation under reduced pressure, giving 499.75 g of a carboxylic acid [$H(CF_2)_6COOH$] in high purity (99 g.c. % or higher) with an isolation yield of 65.26 mole %.

EXAMPLE 2
(A Case in which a Fluoroalkyl Group Having a Long Chain was Used)

$H(CF_2)_8CH_2OH$ (500.00 g, 1.16 moles), 55% nitric acid (132.87 g, 1.16 moles) and $FeCl_2.nH_2O$ (0.0050 g) were placed into the autoclave used in Example 1. The mixture was heated with stirring in the same manner as in Example 1. 3.8 hours after the start of heating, the reaction temperature rose to 125° C. and the reaction pressure increased to 0.8 MPa. From that time, oxygen was fed into the gas phase in the same manner as in Example 1, whereby the reaction pressure was controlled at 0.8 MPa. 7.0 hours after the start of heating, complete consumption of the starting fluoroalkyl alcohol was confirmed by gas chromatography to confirm the completion of the reaction [$H(CF_2)_8CH_2OH$ conversion: 100.0 g.c. %; $H(CF_2)_8COOH$ selectivity: 99.6 g.c. %]. The same procedure as in Example 1 was followed and 651.93 g of a crude carboxylic acid [$H(CF_2)_8COOH$] was obtained in a concentrated form from the lower layer by means of liquid-liquid separation. The crude carboxylic acid was purified by distillation under reduced pressure, giving 475.13 g of a carboxylic acid [$H(CF_2)_8COOH$] in high purity (96 g.c. % or higher) with an isolation yield of 72.88 mole %.

EXAMPLE 3
(A Case in which a Fluoroalkylcarboxylic Acid was Added Before Reaction)

$H(CF_2)_8CH_2OH$ (518.40 g, 1.20 moles), $H(CF_2)_8COOH$ (269.60 g, 0.60 mole), 55% nitric acid (137.45 g, 1.20 moles) and $FeCl_2.nH_2O$ (0.0079 g) were placed into the autoclave used in Example 1. The mixture was heated with stirring in the same manner as in Example 1. 2.6 hours after the start of heating, the reaction temperature rose to 125° C. and the reaction pressure increased to 0.6 MPa. From that time. oxygen was fed into the gas phase in the same manner as in Example 1, whereby the reaction pressure was controlled at 0.6 MPa. 5.4 hours after the start of heating, complete consumption of the starting fluoroalkyl alcohol was confirmed by gas chromatography to confirm the completion of the reaction [H(CF$_2$)$_8$CH$_2$OH conversion: 100.0 g.c. %; H(CF$_2$)$_8$COOH selectivity: 99.6 g.c. %]. The same procedure as in Example 1 was followed and 835.36 g of a crude carboxylic acid [H(CF$_2$)$_8$COOH] was obtained in a concentrated form from the lower layer by means of liquid-liquid separation. The crude carboxylic acid was purified by distillation under reduced pressure, providing 586.04 g of a carboxylic acid [H(CF$_2$)$_8$COOH] in high purity (96 g.c. % or higher) with an isolation yield of 72.19 mole %. By subtracting the amount of H(CF$_2$)$_8$COOH originally fed, the amount of H(CF$_2$)$_8$COOH produced in Example 3 was found 392.85 g.

EXAMPLE 4

(A Case of Not Separating into a Nitric Acid Layer and Another Liquid Layer)

CF$_3$CH$_2$OH (200.00 g, 2.00 moles), 55% nitric acid (114.55 g, 1.00 mole) and FeCl$_2$.nH$_2$O (0.0020 g) were placed into the autoclave used in Example 1. The mixture was heated with stirring in the same manner as in Example 1. 3.0 hours after the start of heating, the reaction temperature rose to 125° C. and the reaction pressure increased to 0.75 MPa. From that time, oxygen was fed into the gas phase in the same manner as in Example 1, whereby the reaction pressure was controlled at 0.75 MPa. 6.0 hours after the start of heating, complete consumption of the starting fluoroalkyl alcohol was confirmed by gas chromatography to confirm the completion of the reaction [CF$_3$CH$_2$OH conversion: 100.0 g.c. %; CF$_3$COOH selectivity: 98.5 g.c. % or higher]. The same procedure as in Example 1 was followed, thus giving an aqueous nitric acid solution of CF$_3$COOH (361.18 g, a material balance of 99.43 mass %).

What is claimed is:

1. A process for producing a fluoroalkylcarboxylic acid of the formula RfCOOH wherein Rf is a C$_{1-16}$ fluoroalkyl group, which comprises oxidizing a fluoroalkyl alcohol having a formula H(CF$_2$)$_n$CH$_2$OH or F(CF$_2$)$_n$CH$_2$OH, wherein n is an integer of 1 to 16, using nitric acid and feeding oxygen into the reaction system after the start of the oxidation reaction to reduce the required amount of nitric acid to a stoichiometric amount or less relative to the fluoroalkyl alcohol.

2. The process according to claim 1 wherein the oxidation is carried out in the presence of a metal catalyst.

3. The process according to claim 2 wherein the metal catalyst is at least one metal selected from the group consisting of iron, nickel, copper and vanadium, or at least one oxide or salt of these metals.

4. The process according to claim 1 wherein a fluoroalkylcarboxylic acid of the formula RfCOOH wherein Rf is as defined above is present in the reaction system at the beginning of the reaction.

\* \* \* \* \*